United States Patent [19]

Suarato et al.

[11] 4,438,105
[45] Mar. 20, 1984

[54] 4'-IODODERIVATIVES OF ANTHRACYCLINE GLYCOSIDES

[75] Inventors: Antonino Suarato; Sergio Penco; Federico Arcamone; Anna M. Casazza, all of Milan, Italy

[73] Assignee: Farmaitalia Carlo Erba S.p.A, Milan, Italy

[21] Appl. No.: 368,415

[22] Filed: Apr. 14, 1982

[51] Int. Cl.³ ............... A61K 31/71; C07H 15/24
[52] U.S. Cl. ......................... 424/180; 536/64
[58] Field of Search .................. 536/6.4; 424/180

[56] References Cited

U.S. PATENT DOCUMENTS 4,303,785  12/1981  Umezawa et al. ............... 424/180
4,345,070   8/1982  Suarato et al. .................. 424/180

Primary Examiner—Johnnie R. Brown
Attorney, Agent, or Firm—Oblon, Fisher, Spivak, McClelland & Maier

[57] ABSTRACT

Starting from the known 4'-deoxy-4'-iodo-N-trifluoroacetyldaunorubicin, two new anthracycline glycosidic antibiotics, the 4'-deoxy-4'-iodo-daunorubicin and 4'-deoxy-4'-iodo-doxorubicin, have been prepared by known procedures. Both the new glycosides have been found to be endowed with outstanding antitumoral activity.

5 Claims, No Drawings

4'-IODODERIVATIVES OF ANTHRACYCLINE GLYCOSIDES

The present invention relates to new glycosidic anthracycline antibiotics of the general formula I:

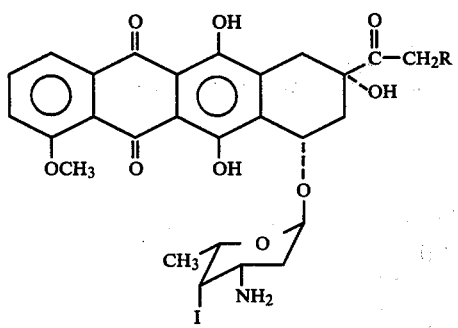

wherein R is a hydrogen atom or a hydroxy group.

Both new glycosides, that is 4'-deoxy-4'-iododaunorubicin and 4'-deoxy-4'-iododoxorubicin, have been found to be endowed with oustanding antitumoral activity. The starting material for their preparation is 4'-deoxy-4'-iodo-N-trifluoroacetyldaunorubicin, an intermediate compound already described in our U.S. patent specification Ser. No. 270,877 (5/6/81).

Mild alkaline hydrolysis of said intermediate with an aqueous solution of 0.1 N NaOH provides the new 4'-deoxy-4'-iododaunorubicin which, by subsequent reaction with bromine is transformed, through its 14-bromo derivative, into its 4'-deoxy-4'-iododoxorubicin analogue.

The new anthracycline glycosides of the invention display antitumor activity. Particularly, 4'-deoxy-4'-iododoxorubicin (I; R=OH) displays remarkable activity on experimentals tumor in mice.

Accordingly, the invention, in yet further aspects, provides pharmaceutical compositions comprising a therapeutically effective amount of an anthracycline glycoside of formula I admixture with a pharmaceutically acceptable diluent or carrier, and methods of treating certain mammalian tumors comprising administering to a host afflicted therewith, therapeutically effective amounts of said compounds.

The invention will now be described in greater detail in the following preparative examples and biological data.

EXAMPLE 1

4'-deoxy-4'-iododaunorubicin (I; R=H) (X00−0138)
A solution of 2.0 g of 4'-iodo-N-trifluoroacetyl daunorubicin in 10 ml of acetone was treated with 80 ml of an aqueous solution of 0.1 N Na OH. After 3 hours at 0° C., the solution was adjusted to pH 4.5 with 0.1 N aqueous HCl and extracted with chloroform in order to eliminate the aglycones.

The aqueous solution was then adjusted to pH 8.6 and extracted with chloroform.

The combined extracts were dried over anhydrous sodium sulfate, concentrated to a small volume and acidified to pH 4.5 with 0.1 N methanolic hydrogen chloride to allow cristallization of the title compound as its hydrochloride. Yield 1.5 g m.p. 157° (dec.); FD-MS: 637 (M+)

TLC on Kieselgel plates $F_{254}$ (Merck) using $CHCl_3$: MeOH: $H_2O$: AcOH (80:20:7:3) v/v) Rf=0.72

EXAMPLE 2

4'-deoxy-4'-iododoxorubicin (I; R=OH) (X00−0163)

A solution of 4'-deoxy-4'-iododaunorubicin in a mixture of methanol and dioxane, in accordance with the method described in U.S. Pat. No. 3,803,124, was treated with bromine to form the 14-bromo derivative, which by treatment with an aqueous solution of sodium formate gave 4'-deoxy-4'-iododoxorubicin which was isolated as hydrochloride.

m.p. 230° C. (dec); FD-MS: 653 (M+)

TLC on Kieselgel plates $F_{254}$ (Merck) using $CHCl_3$: MeOH: $H_2O$: AcOH (80:20:7:3 v/v) Rf=0.5

Biologic activity of compounds X00−0138 and X00−0163

The compounds have been tested in comparison with daunorubicin (DNR) and doxorubicin (DX) against HeLa cells in vitro. Data reported in Table 1 show that X00−0138 was less cytotoxic than DNR, while X00−0163 was more cytotoxic than DX. The antitumor activity was assessed in vivo in mice bearing P388 ascitic leukemia. Results are reported in Table 2. Both the new derivatives are active against P388 leukemia. Of particular interest is the result obtained by treatment of the tumored mice with compound X00−0163: at the optimal, non-toxic dose of 15 mg/kg, X00−163 cured more than 50% of the mice (6/10), and at the dose of 10 mg/kg cured 3/10 mice and procured a remarkably high increase of life span in comparison with controls (205%). Therefore, the antitumor activity of X00−0163 is definitely superior to that of DX, which, at the optimal non-toxic dose of 10 mg/kg, cures only occasionally the tumored mice. Compound X00−138 was also tested against Gross leukemia (treatment in on Day 1 after tumor inoculum). Data reported in Table 3 show that, at the optimal non toxic dose of 11.8 mg/kg, X00−0138 showed in antitumor activity superior to that of DNR, and similar to that of DX.

TABLE 1

| Effect on HeLa cells cloning efficiency[a] | | | |
|---|---|---|---|
| Compound | Dose (ng/ml) | % | $ID_{50}$ (ng/ml) |
| Daunorubicin | 12.5 | 7 | 7 |
|  | 6.25 | 53 |  |
|  | 3.1 | 110 |  |
| X00-0138 | 100 | 0 | 15 |
| 4'-deoxy-4'-iododauno rubicin | 25 | 5 |  |
|  | 6.2 | 109 |  |
| Doxorubicin | 25 | 0 | 8 |
|  | 12.5 | 16 |  |
|  | 6.2 | 70 |  |
| X00-0163 | 25 | 0 | 5.5 |
| 4'-deoxy-4'-iododo xorubicin | 6.2 | 16 |  |
|  | 1.5 | 91 |  |
|  | 0.39 | 104 |  |

[a]Treatment for 24 hours

TABLE 2

| Effect against P 388 ascitic leukemia[a] | | | | |
|---|---|---|---|---|
| Compound | Dose[b] (mg/kg) | T/C[c] % | LTS[d] | Toxic[e] deaths |
| Daunorubicin | 2.9 | 160, 165 | 0/10, 0/10 | 0/10, 0/10 |
|  | 4.4 | 160, 185 | 0/10, 0/10 | 1/10, 0/10 |
|  | 6.6 | 175, 135 | 0/10, 0/10 | 7/10, 7/10 |
| X00-0138 | 4.4 | 140 | 0/10 | 0/10 |
|  | 6.6 | 155 | 1/10 | 0/10 |

TABLE 2-continued

Effect against P 388 ascitic leukemia[a]

| Compound | Dose[b] (mg/kg) | T/C[c] % | LTS[d] | Toxic[e] deaths |
|---|---|---|---|---|
| | 10 | 185, 75 | 0/10, 0/10 | 0/10, 6/10 |
| | 15 | 70 | 0/10 | 8/10 |
| | 22.5 | 60 | 0/10 | 10/10 |
| Doxorubicin | 4.4 | 210 | 0/10 | 0/10 |
| | 6.6 | 260 | 0/10 | 0/10 |
| | 10 | 265 | 1/10 | 0/10 |
| X00-0163 | 6.6 | 240 | 0/10 | 0/10 |
| | 10 | 305 | 3/10 | 0/10 |
| | 15 | >620 | 6/10 | 0/10 |
| | 22.5 | 390 | 3/10 | 1/10 |

[a] Experiments were performed in BDF 1 or CDF 1 mice, inoculated with $10^6$ leukemia cells i.p.
[b] Treatment i.p. on Day 1 after tumor inoculum
[c] Median survival time of treated mice/median survival time of controls, X100
[d] Long term survivors (>60 days)
[e] Evaluated on the basis of autoptic findings.

TABLE 3

Effect against Gross leukemia[a]

| Compound | Dose[b] (mg/kg) | T/C %[c] | LTS[d] | Toxic[e] deaths |
|---|---|---|---|---|
| Daunorubicin | 15 | 191 | 0/8 | 0/8 |
| | 22.5 | 158 | 0/8 | 4/8 |
| Doxorubicin | 7.7 | 150 | 0/10 | 0/10 |
| | 10 | 175 | 0/10 | 0/10 |
| | 13 | 200 | 0/10 | 0/10 |
| | 16.9 | 233 | 0/10 | 0/10 |
| | 22 | 266 | 0/10 | 1/10 |
| X00-0138 | 11.8 | 108 | 0/10 | 0/10 |
| | 15.4 | 208 | 0/10 | 2/10 |
| 4'-iododaunorubicin | 20 | 175, 117 | 0/8, 0/10 | 4/8, 6/10 |
| | 30 | 100 | 0/8 | 8/8 |
| | 40 | 92 | 0/8 | 8/8 |

[a] C3H mice were injected i.v. with $2 \times 10^6$ leukemia cells
[b] Treatment i.v. on Day 1 after tumor inoculum
[c,d,e] see Table 2

What we claim is:

1. An anthracycline glycosidic compound of the general formula I.

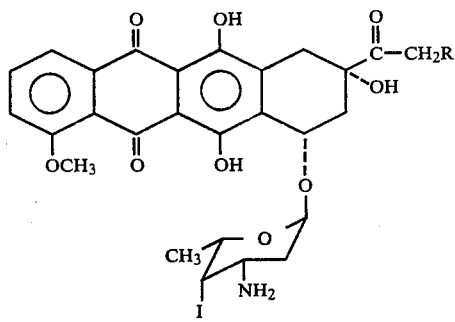

wherein R is a hydrogen atom or a hydroxy group.

2. A compound according to claim 1, which is 4'-deoxy-4'-iododaunorubicin.

3. A compound according to claim 1, which is 4'-deoxy-4'-iododoxorubicin.

4. A pharmaceutical composition having antitumor activity against a tumor selected from the group consisting of P388 leukemia and gross leukemia comprising a therapeutically effective amount of an anthracycline glycoside according to claim 1 in combination with an inert carrier therefor.

5. A method of inhibiting the growth of a tumor selected from the group of P388 leukemia or Gross leukemia, said method comprising administering to a host afflicted with said tumor a therapeutically effective amount of an anthracycline glycoside as claimed in claim 1.

* * * * *